US010811126B2

(12) United States Patent
Warren et al.

(10) Patent No.: US 10,811,126 B2
(45) Date of Patent: Oct. 20, 2020

(54) SYSTEM AND METHODS FOR DEVELOPING AND USING A MICROBIOME-BASED ACTION COMPONENT FOR PATIENT HEALTH

(71) Applicants: Tracy Warren, Pennington, NJ (US);
Tammi Jantzen, Platteville, WI (US);
Katherine Gregory, Arlington, MA (US)

(72) Inventors: Tracy Warren, Pennington, NJ (US);
Tammi Jantzen, Platteville, WI (US);
Katherine Gregory, Arlington, MA (US)

( * ) Notice: Subject to any disclaimer, the term of this patent is extended or adjusted under 35 U.S.C. 154(b) by 197 days.

(21) Appl. No.: 15/842,346

(22) Filed: Dec. 14, 2017

(65) Prior Publication Data

US 2018/0166165 A1 Jun. 14, 2018

Related U.S. Application Data

(60) Provisional application No. 62/433,990, filed on Dec. 14, 2016.

(51) Int. Cl.
  *G16H 20/10* (2018.01)
  *G16H 50/30* (2018.01)
  *G16H 20/60* (2018.01)

(52) U.S. Cl.
  CPC ............ *G16H 20/10* (2018.01); *G16H 20/60* (2018.01); *G16H 50/30* (2018.01)

(58) Field of Classification Search
  CPC .. G16H 10/00–80/00; G06F 1/00–1/26; A61B 1/00–2576/026; C12Q 1/00–2600/178
  See application file for complete search history.

(56) References Cited

U.S. PATENT DOCUMENTS 9,058,627 B1 * 6/2015 Wasser ................. G06F 3/0488
2004/0214148 A1 * 10/2004 Salvino ..................... A61N 1/39
                                                           434/262

(Continued)

FOREIGN PATENT DOCUMENTS

WO      2011130546 A1    10/2011

OTHER PUBLICATIONS

Forslund et al., "Disentangling type 2 diabetes and metformin treatment signatures in the human gut microbiota ," Dec. 2015, Nature, vol. 528—dated Dec. 10, 2015.*

(Continued)

*Primary Examiner* — Elaine Gort
*Assistant Examiner* — Jonathon A. Szumny
(74) *Attorney, Agent, or Firm* — Valauskas Corder LLC

(57) ABSTRACT

The invention relates generally to a system and methods by which a microbiome-based action component may be developed that is useful in order to establish, restore, promote, or maintain patient health. More specifically, the system and methods of the present invention may be used to develop a microbiome-based action component that efficiently summarizes the state of a patient's microbiome and whether and to what extent inflammation exists in the patient's intestines. Such an efficient summary may be used to render more immediate health care to the patient. Certain specific embodiments of the present invention may be used to facilitate the development a microbiome-based action component that provides, in addition to the efficient summary, a patient-specific, personalized microbiome health plan that includes options that may be followed in order that the patient may achieve personal health, growth, and development goals given the state of the patient's microbiome and intestinal inflammation.

7 Claims, 11 Drawing Sheets

(56) References Cited

U.S. PATENT DOCUMENTS

| | | | | |
|---|---|---|---|---|
| 2004/0249675 | A1* | 12/2004 | Stark | A61H 1/00 705/2 |
| 2008/0167262 | A1* | 7/2008 | Cooney | A61K 31/70 514/44 R |
| 2008/0255069 | A1* | 10/2008 | Shudo | A61K 31/192 514/63 |
| 2010/0004213 | A1* | 1/2010 | Abbas | A61K 31/56 514/166 |
| 2010/0015156 | A1* | 1/2010 | Dubinsky | C12Q 1/6883 424/139.1 |
| 2012/0171672 | A1* | 7/2012 | Barken | C12Q 1/6883 435/6.11 |
| 2012/0296675 | A1* | 11/2012 | Silverman | G06Q 50/22 705/3 |
| 2013/0035951 | A1* | 2/2013 | Frey | G16H 50/30 705/2 |
| 2013/0225439 | A1* | 8/2013 | Princen | C12Q 1/6883 506/9 |
| 2014/0179726 | A1 | 6/2014 | Bajaj et al. | |
| 2014/0314719 | A1* | 10/2014 | Smith | A61K 35/747 424/93.3 |
| 2014/0358587 | A1* | 12/2014 | Cao | A61B 5/747 705/3 |
| 2016/0071393 | A1* | 3/2016 | Kaplan | A61B 5/6831 340/539.12 |
| 2016/0139148 | A1* | 5/2016 | Westin | G01N 33/6893 506/9 |
| 2016/0178644 | A1* | 6/2016 | Hackney | C12Q 1/6883 424/136.1 |
| 2016/0216274 | A1* | 7/2016 | Kain | G01N 33/6842 |
| 2016/0245786 | A1* | 8/2016 | Collino | G01N 33/6893 |
| 2016/0266147 | A1* | 9/2016 | Loktionov | G01N 33/6893 |
| 2016/0314281 | A1 | 10/2016 | Apte et al. | |
| 2017/0202925 | A1* | 7/2017 | Couvineau | A61K 45/06 |
| 2017/0205429 | A1* | 7/2017 | Figeys | A61K 45/06 |
| 2018/0010187 | A1* | 1/2018 | Lyons | C12Q 1/6883 |
| 2018/0022800 | A1* | 1/2018 | West | C07K 16/248 424/133.1 |
| 2018/0046774 | A1* | 2/2018 | Lindahl | A61B 5/42 |
| 2018/0064950 | A1* | 3/2018 | Segal | A61N 2/006 |
| 2018/0180630 | A1* | 6/2018 | Monteleone | G01N 33/6863 |
| 2019/0030096 | A1* | 1/2019 | Cutcliffe | G01N 33/66 |

OTHER PUBLICATIONS

Bokulich et al., "Antibiotics, birth mode, and diet shape microbiome maturation during early life," Jun. 15, 2016, Science Translations Medicine, vol. 8, Issue 343. (Year: 2016).*

* cited by examiner

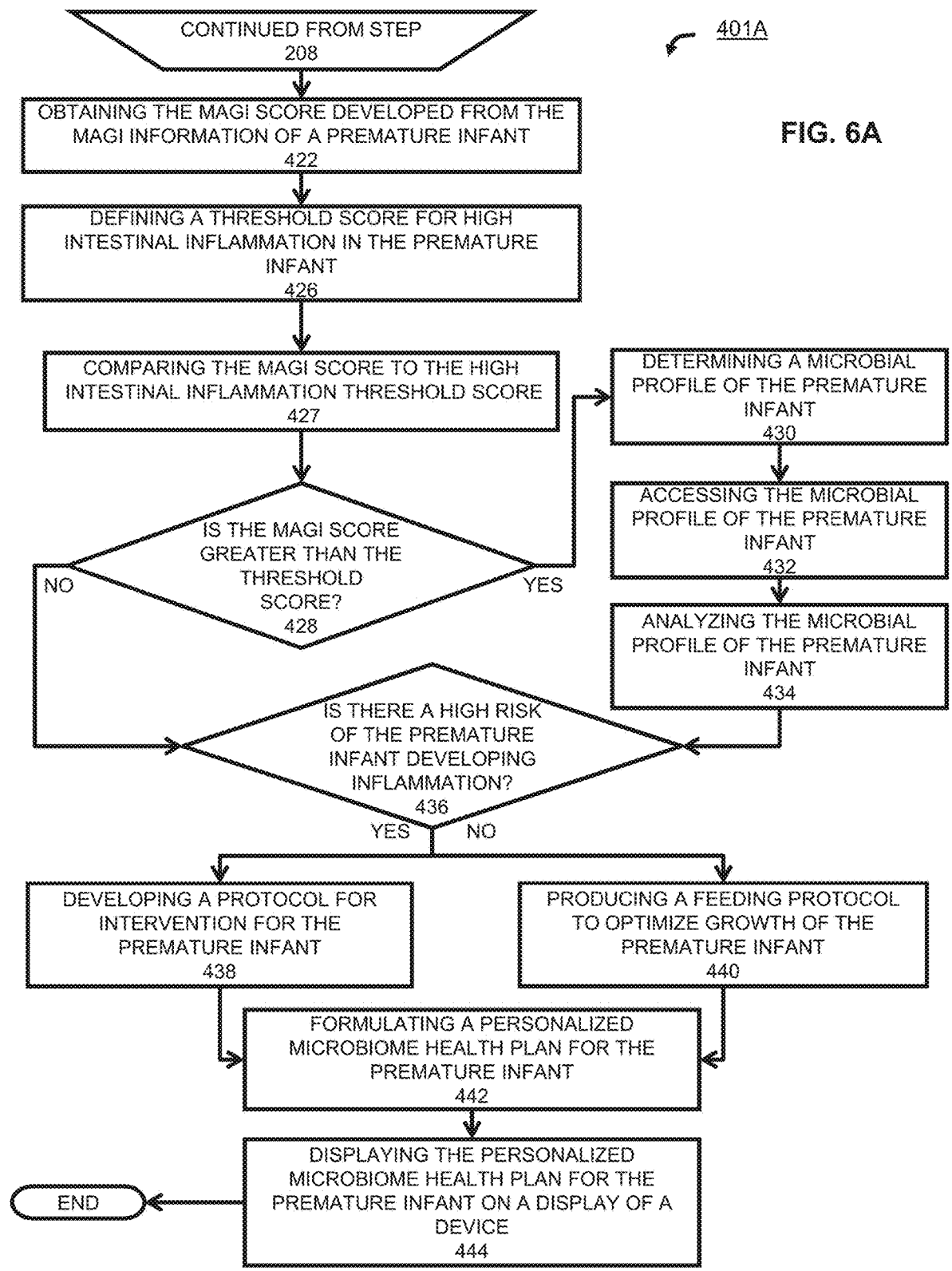

SYSTEM AND METHODS FOR DEVELOPING AND USING A MICROBIOME-BASED ACTION COMPONENT FOR PATIENT HEALTH

CROSS REFERENCE TO RELATED PATENTS

This application claims the benefit of U.S. Provisional Patent Application No. 62/433,990 filed Dec. 14, 2016, which is incorporated by reference.

FIELD OF INVENTION

The field of invention relates generally to a system and methods that may be used to develop a microbiome-based action component useful to establish, promote, or maintain patient health. More specifically, the system and methods of the present invention may be used to develop a microbiome-based action component that efficiently summarizes the state of a patient's microbiome and whether and to what extent inflammation exists in the patient's intestines. Such an efficient summary may be used to render more immediate health care to the patient. Certain specific embodiments of the present invention may be used to develop a microbiome-based action component that provides, in addition to the efficient summary, a patient-specific, personalized microbiome health plan that includes options that may be followed in order that the patient may achieve personal health, growth, and development goals given the state of the patient's microbiome and intestinal inflammation.

BACKGROUND OF THE INVENTION

A microbe is a single-celled or multicellular microscopic living organism. There are six main types of microbes: archaea, bacteria, fungi, protozoa, viruses, and algae. Microbes live in practically every part of the biosphere and are found everywhere in and on the human body, including the nasal passages, oral cavities, skin, gastrointestinal tract, and the urogenital tract. The term "microbiota" refers to a community of commensal, symbiotic, and/or pathogenic microbes. The term "microbiome" refers to the full collection of microbes and the genetic information of those microbes within a specific body area (the "habitat") of the host.

Each type of microbe may produce a different effect in the context in which the microbe comes to live. The composition of the microbiota that may reside on and within, for example, a mammalian organism may affect immune function, nutrient processing, and other aspects of physiology. The composition of the microbiota may change over time and can be affected by age, diet, antibiotic exposure, and other environmental influences. When different microbial species produce largely the same effect, the microbiota is said to have some functional redundancy. An addition or loss of microbial species that produce similar effects may have little influence on the overall effect that the microbiota has on the physiology of the mammalian system. However, the addition or loss of certain microbial species, even if present in small numbers, may produce a significant effect on mammalian physiology.

When the microbial species that produce what is considered to be a beneficial effect on the system are not at least equal to the microbial species that produce what is considered to be a harmful effect on the system, a microbial imbalance is said to have been created. "Dysbiosis" refers to the state in which a system has an imbalance in the beneficial and harmful microbes. Dysbiosis can occur when there is a low diversity of beneficial microbial species and/or a lack of functional redundancy of beneficial microbes in the microbiota.

What is considered to be a healthier system may be established or reestablished by limiting the harmful microbes while promoting the development of the beneficial microbes. The term "eubiosis" refers to the state in which the beneficial microbes within a system have a dominant effect because there is a high diversity and/or a functional redundancy of the beneficial microbial species in the system.

Throughout the animal kingdom, females can transfer microbes to a fetus before birth and to their offspring during the course of and after birth. Several factors, including method of birth, the environment in which the birth takes place, and manner of feeding can influence the precise microbial community associated with a newborn. In addition to factors relevant to labor and birth, females can transfer microbes to a fetus and to their offspring in many ways. For example, microbes can become associated with a fetus in the prenatal phase. The placenta harbors a variety of microbes to which the fetus is exposed. As the fetus passes through the birth canal, it is exposed to the microbes of the mother's vagina. After birth, skin-to-skin contact can transfer microbes from mother to infant. Also, microbes in breast milk are passed to the infant during feeding. All such early exposures to microbes influence the developing immune system of the infant, and ultimately affect the individual's health throughout childhood and later in life.

The fetus and newborn develop certain microbial communities depending on whether the child is born after a full-term pregnancy. Premature infants, as a result of the early birth, have a microbial community that is highly influenced by the shorter gestation period and the hospitalized environment where life-saving intensive care was rendered to the infant following birth. The microbiome of such infants is often less fully developed and may include the harmful or pathogenic species found in the hospital environment. An underdeveloped microbiota in and/or on the premature infant may lead to a dominance of deleterious microbes and disease. For example, premature infants in a dysbiotic state may develop a serious gastrointestinal infection called necrotizing enterocolitis ("NEC"). This disease is just one example of the many child health outcomes that are associated with early microbial and immune-mediated mechanisms.

Given the consequences, there are many advantages in analyzing which microbes are associated with a premature infant at an early age in order, for example, to determine whether the infant may be suffering from a condition caused by harmful or pathogenic microbes—such as an unhealthy inflamed state—and whether the infant may be in a dysbiotic state. Even after such early age, there are many advantages in determining the state of an older patient's microbiome and whether the patient is suffering from inflammation.

The microbes associated with a premature infant or any patient can be identified in many ways. For example, certain microbial species that reside on and within a patient may be identified by collecting samples from the microbiota and culturing them in an appropriate culture media. Such a traditional culture-based method, however, can detect only those microbes that can be grown in vitro. As a result, other culture-independent methods, such as molecular genomic sequencing, have been developed to analyze the genetic material of a microbiota sample and detect those microbes that were previously undetectable by traditional, culture-based methods.

While many benefits can be realized from the analysis of a patient's microbial state, such analyses are not currently conducted as part of standard clinical care procedures. Current care protocols react to a patient's physical signs caused by conditions, including those caused by an imbalance of the patient's microbiota and inflammation. Such reactive treatments for conditions caused by microbiota imbalances include withholding feedings, bowel rest, and antibiotic administration. These treatments often take time to produce results and may have many unintended risks associated with them for the patient.

Even when the microbial condition of a patient is identified, the important question of whether and to what extent the patient is suffering from inflammation may not be answered.

Treatment to improve, maintain, and advance the health condition of a patient could be more efficiently rendered if an efficient summary of the patient's microbial condition, and whether and to what extent the patient is suffering from inflammation was available.

Furthermore, a comprehensive approach to the care of a patient that takes into account the patient's microbial state and inflammation state and seeks to achieve a range of short-term and longer term, health-related objectives, such as promoting the growth and development of the patient, would be advantageous to a patient.

However, any such microbiome-based action component has not been developed and, as a result, is not available for use as part of conventional standard of care protocols.

Accordingly, there is a need for a system and methods by which a microbiome-based action component may be developed and made available for use for patient health and that may be revised as the condition of the patient changes. The present invention satisfies this need.

SUMMARY OF THE INVENTION

The present invention relates generally to a system and methods that may be used to develop a microbiome-based action component useful to establish, promote, and maintain patient health. More specifically, the system and methods of the present invention may be used to develop a microbiome-based action component that efficiently summarizes the state of a patient's microbiome and whether and to what extent inflammation exists in the patient's intestines. Such an efficient summary may be made accessible to a patient and health care providers and used to render more immediate care to the patient. Certain preferred embodiments of the present invention may be used to develop a microbiome-based action component that provides, in addition to the efficient summary, a patient-specific, personalized microbiome health plan that includes options that may be followed in order that the patient may achieve personal health, growth, and development goals given the state of the patient's microbiome and intestinal inflammation. For purposes of this application, a "patient" is any mammal. Illustrative examples in the following include those making reference to humans.

Certain preferred embodiments of the present invention permit a patient to supply some or all the data needed by the system to develop the microbiome-based action component, not only by entry of such information by the patient directly but also through the use of a device such as a wearable or insertable device that can communicate to the system and/or from other sources such as the patient's health records. Other preferred embodiments are intended to be used by a health care provider and permit such individual to incorporate information provided directly by the patient or from observations made, analyses conducted, and/or treatments rendered by the health care provider or third parties and recorded such as in the health care records for the patient.

In certain preferred embodiments of the invention, the system may be used to develop a microbiome-based action component that provides a summary of the state of the patient's microbiome and gut inflammation. This microbiome-based action component is based on the" microbiome and gut inflammation"—or "MAGI"—information received for a patient. In certain embodiments, this system develops the MAGI information through the following steps: identifying the patient; identifying the health risk factors for the patient; obtaining the clinical information of the patient; making adjustments to the data if the patient is a premature infant; and determining a gut inflammation level for the patient using a biochemical and/or genetic marker. The system may update and revise the MAGI information as the data and other inputs change or as selections are made. From the MAGI information, the system develops a summary that allows the patient's microbiome and inflammation state to be understood quickly and for treatment options to be selected. This microbiome-based action component is termed a MAGI score for purposes of this application.

In certain preferred embodiments, the above two steps may be followed by a third step in which an additional microbiome-based action component—a personalized microbiome health plan—may be created for the patient based on the MAGI score. This plan may identify options that a health care provider may follow to achieve patient-specific objectives. Among other options, a health care provider may choose to develop a nutritional plan for the patient, recommend that the patient change or adopt a certain hygiene plan, modify sleep patterns, take steps to engage in certain exercise, and generally modify other behaviors.

More specifically regarding the collection and development of the MAGI information described above, the patient is identified such as by the entry of the patient's name, age, address, and other identifying characteristics. If the patient is a premature infant, the gestational age may be entered as the age of the patient by access to the clinical information of the patient.

In certain preferred embodiments, the MAGI information is developed with the entry of microbial health risk factors. These factors are those conditions or events that may have produced the current microbial condition of the patient. Microbial health risk factors may include the patient's mode of birth (i.e. vaginal or cesarean section), exposure to antibiotics, and the nutrition that the patient is receiving.

The MAGI information may be developed through the entry of clinical information—such as the patient's physical condition, symptoms, and health risk factor information—such as by the patient directly and/or by a health care worker from the patient's medical records, and stored, such as in a server. In certain embodiments, the clinical information may be collected from data repositories, such as electronic health records (EHR) databases, hospital records databases, other patient file databases, Internet databases, and the like and alternatively may be obtained through the use of surveys and questionnaires. Data repositories may be stored in one or more non-transitory data storage devices, such as, but not limited to, those described below with reference to FIG. 9 and FIG. 10. For purposes of this application, clinical information may include a summary of the patient's physical condition, symptoms, and health risk factor information. Symptoms may include an increase in abdominal girth, change in stooling pattern, signs of feeding intolerance, increase in oxygen requirements, an increase in apnea, low respiratory rate, and low heart rate. Clinical information may also include any other information relating to the patient's health, maternal information, and/or development. Maternal information may include the race, antibiotic exposure, and any other health information of the patient's mother prior to birth. Certain preferred embodiments permit the clinical information to be compared to national standards in order to place the patient's development in some additional context. In certain preferred embodiments, the clinical information is stored such that it may be readily retrieved from the server and/or input on a device by a user. The clinical information may be modified as needed.

If the patient is identified as a premature infant in the earlier identification step, the gestational age of the patient is entered as the age of the patient.

In certain preferred embodiments, the inflammation state of the patient's gut is determined. Procedures that provide a biochemical and/or genetic marker of the inflammation state may be utilized.

When available, microbial sequence information may be prepared for the patient. A variety of microbial sequencing methods may be used, including shotgun metagenomics sequencing, rRNA sequencing, and microbial metatranscriptomics. The microbial sequence information may be loaded into the server. In certain preferred embodiments of the invention, the MAGI information may be revised based on the microbial sequence information.

In certain preferred embodiments of the invention, microbiome information of the patient may be developed through the collection of samples from the patient, such as biological samples of patient saliva, blood, tissue, stool, or any other biological material. The analysis of the samples and other information will permit the patient's microbiome to be determined and microbiome information developed. The microbiome information may be stored such that it may be readily retrieved from the server. In certain embodiments, the microbiome information will be stored with the clinical information. In certain preferred embodiments, a biochemical and/or genetic marker, such as an intestinal fatty acid-binding protein, may be used to identify intestinal inflammation in patients.

In certain preferred embodiments, new clinical information corresponding to the patient's mode of birth, treatment, gestational age, nutritional exposure, and the patient's antibiotic exposure may be identified and used to revise the MAGI information.

In certain preferred embodiments of the invention, a MAGI score is calculated using all or a limited amount of MAGI information. For example, a patient's mode of birth may be a factor for an infant. If the patient is not an infant, the mode of birth may or may not be taken into account as a factor when calculating the MAGI score. In another example, gestational age of a patient may be necessary only if the patient is a premature infant.

In certain preferred embodiments of the invention, a risk of a patient developing an inflammatory disease may be predicted based on the MAGI score. In certain preferred embodiments, a range of MAGI scores may be defined to categorize a risk for the patient. For example, a range of 1 through 10 may be used, such that a patient with a MAGI score of 1-3 is associated with a low risk of developing an inflammatory disease, a patient with a MAGI score of 4-6 is associated with a moderate risk of developing an inflammatory disease, and a patient with a MAGI score of 7-10 is associated with a high risk of developing an inflammatory disease. Each category of risk (i.e. low, moderate, and high) may have a predefined range of MAGI scores. The predefined ranges may be changed by a user. For example, the user may define the range for a high risk of developing gut inflammation to encompass MAGI scores of 5 through 10. In certain embodiments, the system may prompt the user to define the range for each category of risk.

In certain preferred embodiments of the invention, a risk of a patient developing gut inflammation may be predicted. A threshold score associated with a risk of gut inflammation may be defined. The gut inflammation threshold score may be a minimum MAGI score associated with gut inflammation. In certain embodiments, the method may include predicting a gut inflammation risk level for the patient by using the MAGI score. The MAGI score may be compared to the gut inflammation threshold score in order to determine the gut inflammation risk level. For example, if the MAGI score is determined to be 8 points and the gut inflammation threshold score is determined to be 10 points, the gut inflammation risk level may be high (i.e. greater than 50%).

In certain preferred embodiments of the invention, a plurality of protocols may be prepared for a plurality of MAGI scores. The plurality of protocols for the plurality of MAGI scores may be stored such that protocols may be readily retrieved from the system. For purposes of this application, a protocol may encompass plans, procedures, and rules for treating the patient. For example, a protocol may include rules and procedures applicable to the patient, such as, but not limited to, treatment procedures, nutritional plans, microbial interventions, and antibiotic exposure.

In certain preferred embodiments of the invention, a personalized microbiome health plan may be developed based on the MAGI score for patients with gut inflammation and/or patients at a risk of developing inflammatory diseases. At least one protocol corresponding to the MAGI score may be obtained from the system. The personalized microbiome health plan may include one or more procedures and/or treatments for the relevant microbe-based disease or diseases, such as gut inflammation.

In certain preferred embodiments of the invention, patient results are monitored in order to determine a patient's health status after execution of a protocol. In certain preferred embodiments, the system may process data associated with a patient result that has been input into the system and store the data in the server. Patient results may include protocols used, response to treatment, recovery time, nutritional information, and microbiome information. The system may monitor the patient results to determine if a patient's health has improved after execution of a particular protocol. An improved patient status may be based on an analysis of the patient's microbiome.

In certain preferred embodiments, the system may provide information regarding the effectiveness of a protocol. The system may analyze at least one protocol associated with the patient's health status. An effective protocol may include a protocol that is associated with a personalized microbiome health plan corresponding to an improved patient health state. In certain embodiments, the system may determine that a protocol is not effective and update the information regarding the effectiveness of the protocol to indicate that the protocol was not associated with a personalized microbiome health plan corresponding to an improved patient health state.

In certain preferred embodiments of the invention, the personalized microbiome health plan for the patient may be provided on a display of the system. The display may obtain the MAGI score from the server in response to receiving a request for a MAGI score. The server may send the one or more protocols corresponding to the received MAGI score to the display. In certain embodiments, the server of the system of the present invention may be any suitable server, and can include a network cloud server for storage and sharing of content across multiple systems.

While the invention is susceptible to various modifications and alternative forms, specific exemplary embodiments are shown by way of example in the following drawings which are described in detail. It should be understood, however, that there is no intent to limit the invention to the particular embodiments disclosed. On the contrary, the intention is to cover all modifications, equivalents, and alternatives falling within the scope of the invention as defined by the appended claims.

BRIEF DESCRIPTION OF THE DRAWINGS

FIG. 6A a flow chart illustrating the steps of a certain preferred embodiment of the present invention by which a personalized microbial health plan may be developed and displayed for a premature infant.

DETAILED DESCRIPTION OF THE INVENTION

The present invention relates generally to a system and methods by which a microbiome-based action component may be developed that is useful to establish, restore, promote, and/or maintain patient health. More specifically, the system and methods of the present invention may be used to develop a microbiome-based action component that efficiently summarizes the state of a patient's microbiome and whether and to what extent inflammation exists in the patient's intestines. Such an efficient summary may be used to render more immediate health care to the patient. Certain specific embodiments of the present invention may be used to facilitate the development a microbiome-based action component that provides, in addition to the efficient summary, a patient-specific, personalized microbiome health plan that includes options that may be followed in order that the patient may achieve personal health, growth, and development goals given the state of the patient's microbiome and intestinal inflammation.

Figure 1:
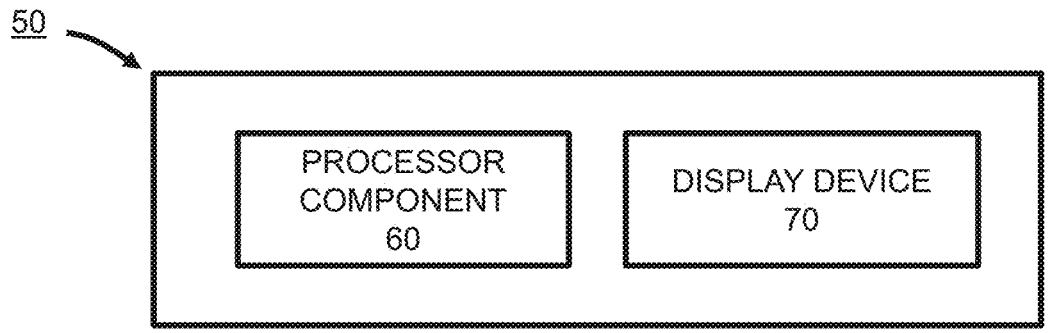
FIG. 1 is a block diagram illustrating a system that may be used to implement one or more methods of the invention.

In the drawings, where like numerals represent like components, FIG. 1 is a block diagram illustration of a system 50 according to one preferred embodiment of the invention. FIG. 1 includes at least a processor component 60 and a display device 70. The processor component 60 executes the instructions of the invention for developing the MAGI information of a patient and, through the use of that information, calculating a MAGI score for the patient and other components described below.

In certain preferred embodiments of the present invention, the processor 60 may process the MAGI score and, with other information, develop a personalized microbiome health plan based on the MAGI score of the patient. The system 50 may provide one or more default arrangements for displaying the MAGI score and/or the personalized microbiome health plan on the display device 70. For example, the system 50 may be configured to provide a display of the patient's MAGI score, the patient's personalized microbiome health plan, or both. The system 50 may also be configurable to revise the MAGI score and/or personalized microbiome health plan in line with updated MAGI information.

A display device 70 can be used to communicate the MAGI score and/or personalized microbiome health plan in visual, audible, or tactile form, and may include, for example, a monitor or touch screen. The display device 70 may provide various types of additional content—such as an image, a moving picture, a text, music, a graphic user interface ("GUI"), an application execution screen, and the like—in addition to the MAGI score and/or personalized microbiome health plan. In certain preferred embodiments, the display device 70 may display a user interface screen that facilitates configuration of system 50 by a user including through the use of at least one selected from an input component such as a keypad, a touch pad, touch screen, a list menu, and an input window. Display device 70 may further recognize interactions that may not involve touch. For example, display device 70 may include a variety of input devices (not shown), such as a camera, and/or microphone, to detect various inputs (e.g. user audio, user gestures, barcodes, etc.). Some examples of the display device 70 may be or may include a liquid crystal display ("LCD") panel, an organic light-emitting diode ("OLED"), and the like.

Figure 2A:
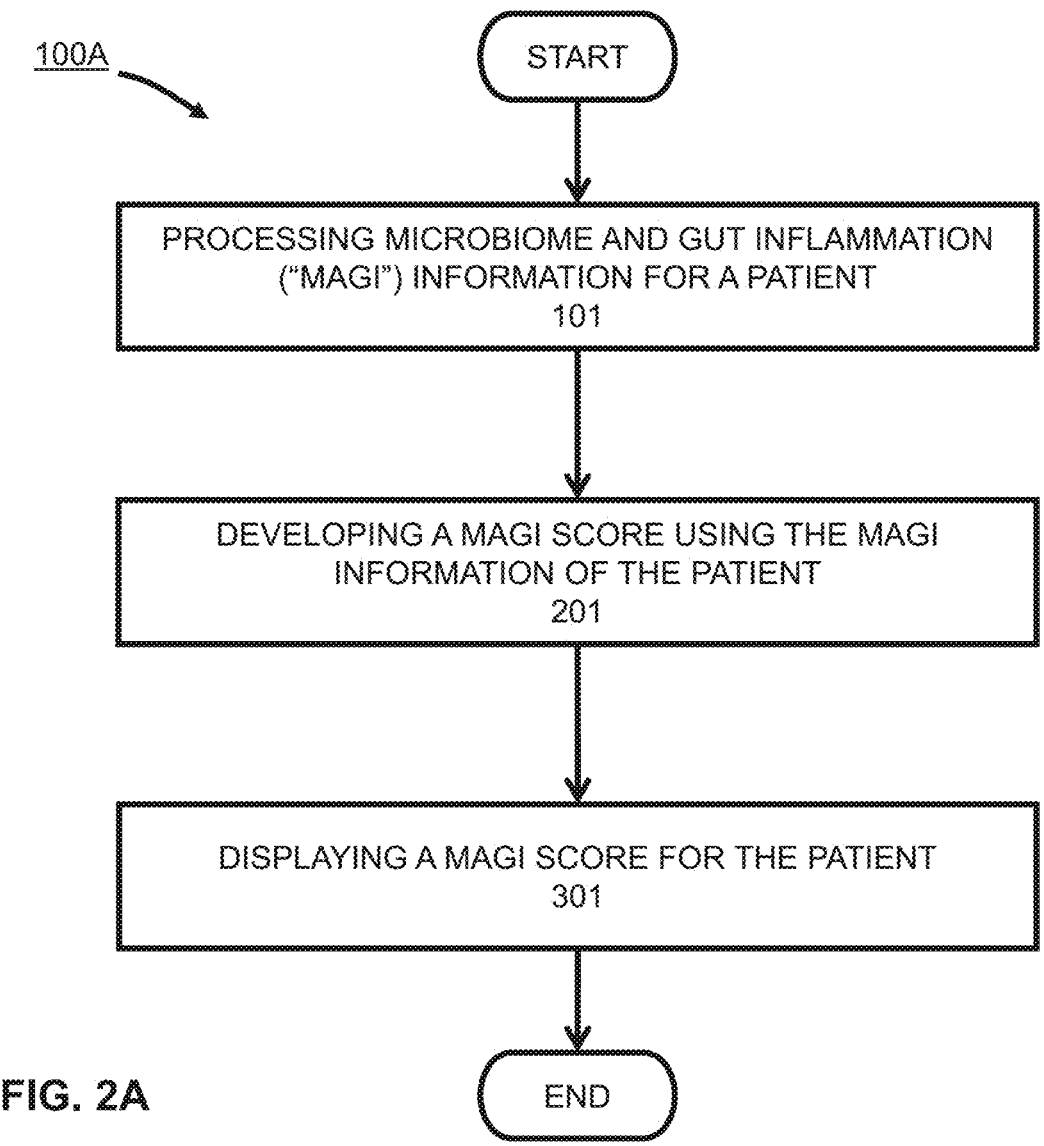
FIG. 2A is a flow chart illustrating the steps of one certain preferred embodiment of a method of the present invention by which one microbiome-based action component—a MAGI score—may be developed.

FIG. 2A is a flowchart 100 illustrating the steps of one certain preferred embodiment of a method according to the present invention by which one microbiome-based action component—the MAGI score—may be developed. The method of operation begins and, in step 101, the microbiome and gut inflammation ("MAGI") information of a patient is accessed. In step 201, a MAGI score is calculated using the MAGI information of the patient. In step 301, a personalized plan for the patient is output.

Figure 2B:
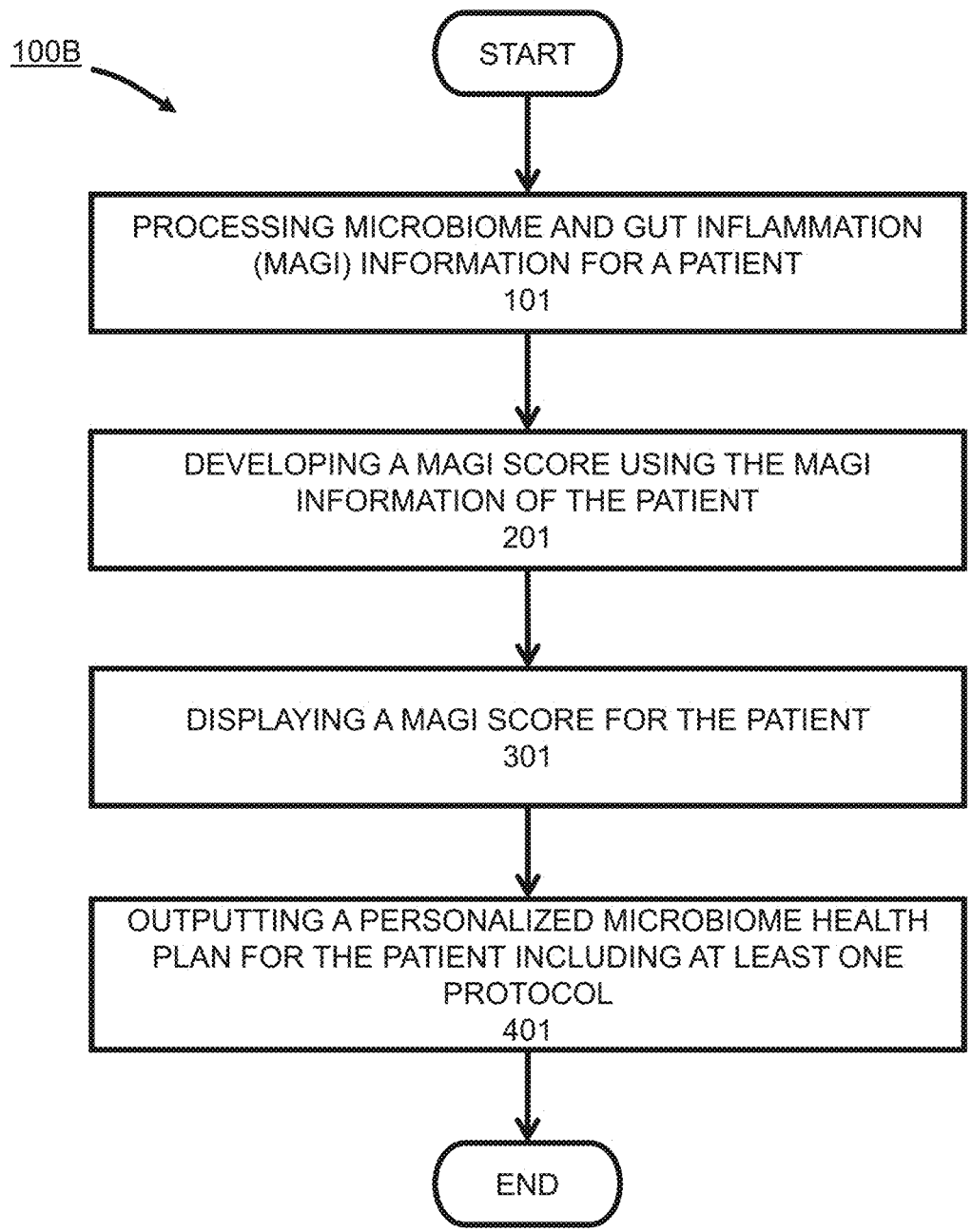
FIG. 2B is a flow chart illustrating the steps of another certain preferred embodiment of a method of the present invention by which an additional microbiome-based action component—a personalized microbiome health plan—may be developed.

FIG. 2B is a flow chart illustrating the steps of another certain preferred embodiment of a method according to the present invention by which an additional microbiome-based action component—a personalized microbiome health plan—may be developed based on the MAGI score. The certain embodiment illustrated in FIG. 2B provides the personalized microbiome health plan with at least one health protocol for the patient in step 401.

FIG. 3 through FIG. 6B illustrate flowcharts further detailing the exemplary operation of certain embodiments of the system 50 illustrated in FIG. 2A and FIG. 2B.

Figure 3:
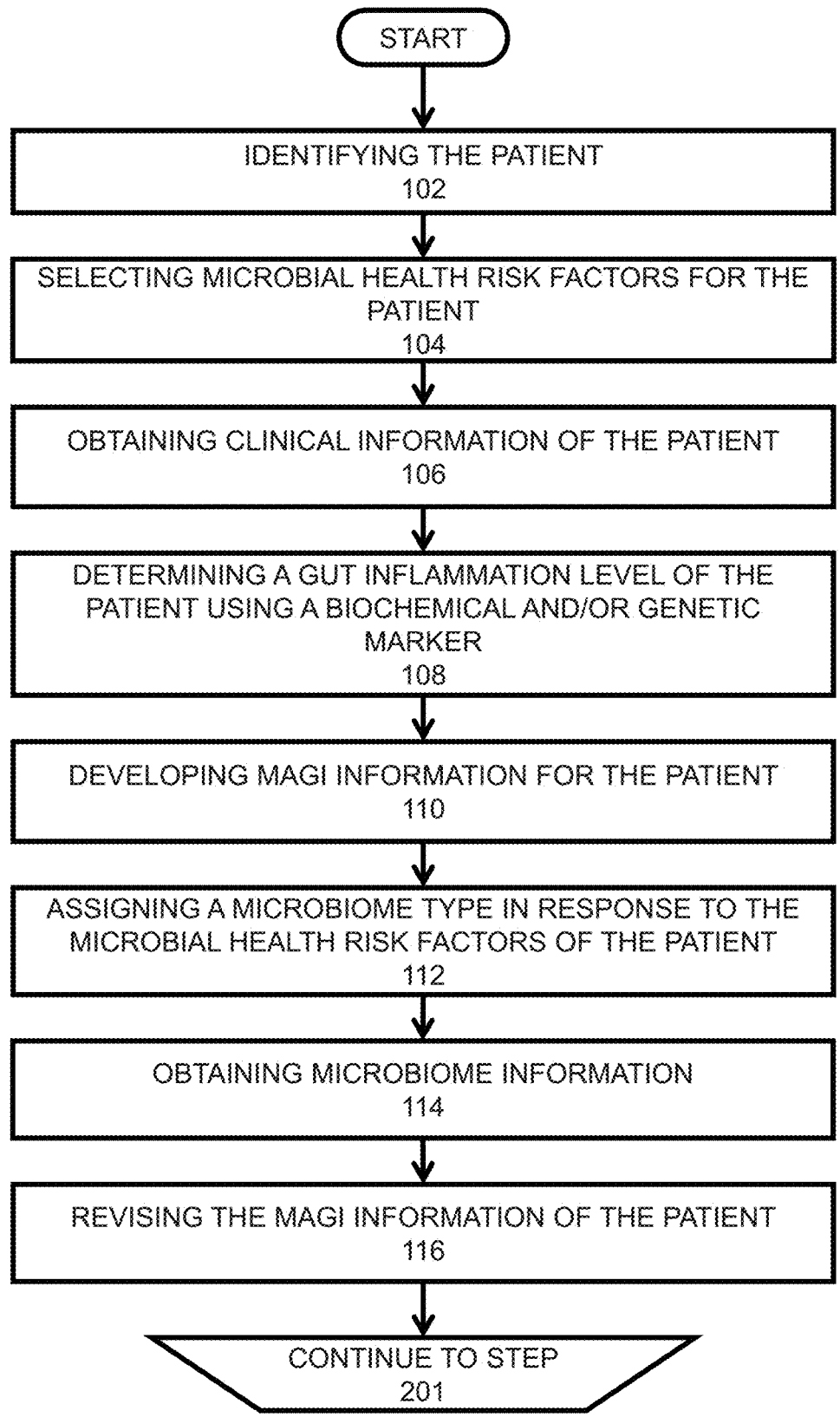
FIG. 3 is a flow chart illustrating the steps of a certain preferred embodiment of a method of the present invention by which the MAGI information may be developed.

FIG. 3 is a flowchart 101 showing the steps of a certain preferred embodiment of a method according to the present invention by which the MAGI information may be developed for the operation of the embodiments of the systems identified as step 101 in FIG. 2A and FIG. 2B. After the operation begins, the patient is identified in step 102. The patient may be any mammal, but the examples discussed in this application make reference to humans. Once the patient is identified, in step 104, microbial health risk factors of the patient will be selected. Microbial health risk factors may include the patient's mode of birth (i.e. vaginal or cesarean section), perinatal risk factors such as maternal body mass index, exposure to antibiotics and the nutrition the patient is receiving or the patient's diet. If the patient is preterm, the microbial health risk factors may include the gestational age of the patient at birth. Microbial health risk factors may be stored in any server accessible to the system 50.

In step 106 of the certain illustrated embodiment, clinical information of the patient is obtained. Clinical information may be stored in any server accessible to the system 50. The clinical information of a patient may be organized according to date, priority of condition, or other technique for organizing data. In step 108, a gut inflammation level of the patient is determined using a biochemical or genetic marker. In some embodiments, the biochemical marker may be an intestinal fatty acid binding-protein ("iFABP") that measures intestinal cell damage. Damaged cells may be characterized histologically by the absence or low presence of fatty acid binding-protein which also facilitate recognition of areas of damaged cells. A high iFABP level may be associated with a dysbiotic state. iFABP may be used for predicting the risk of inflammatory diseases, such as necrotizing enterocolitis ("NEC") or Crohn's disease, that are occurring in the patient. After determining the gut inflammation level at step 108, in step 110, MAGI information for the patient is developed advantageously from some or all information within a wide range of information that may include the clinical information of the patient such as, but not limited to, the symptoms, microbial health risks and gut inflammation levels, and other information of a patient, such as the patient's age (or in the case of a premature patient, adjusted gestational age), the symptoms, mode of birth, nutrition exposure, and antibiotic exposure.

In step 112, a microbiome profile will be assigned in response to the microbial health risk factors of the patient. The microbiome profile may be used to characterize and/or validate the microbiome information for the patient based on the microbial health risk factors. In some embodiments, when the microbial sequence information is available, confirmation of the microbiome profile may be validated.

In step 114, microbiome information of the patient is obtained. Microbiome information may include historic microbiome information, real-time-based microbiome information, derived microbiome information, predictive microbiome information, and combinations thereof.

In step 116, the MAGI information may be revised for the patient. In order to produce a microbiome-based action component, the operation continues to step 201 shown also in FIG. 2A and FIG. 2B.

Figure 4:
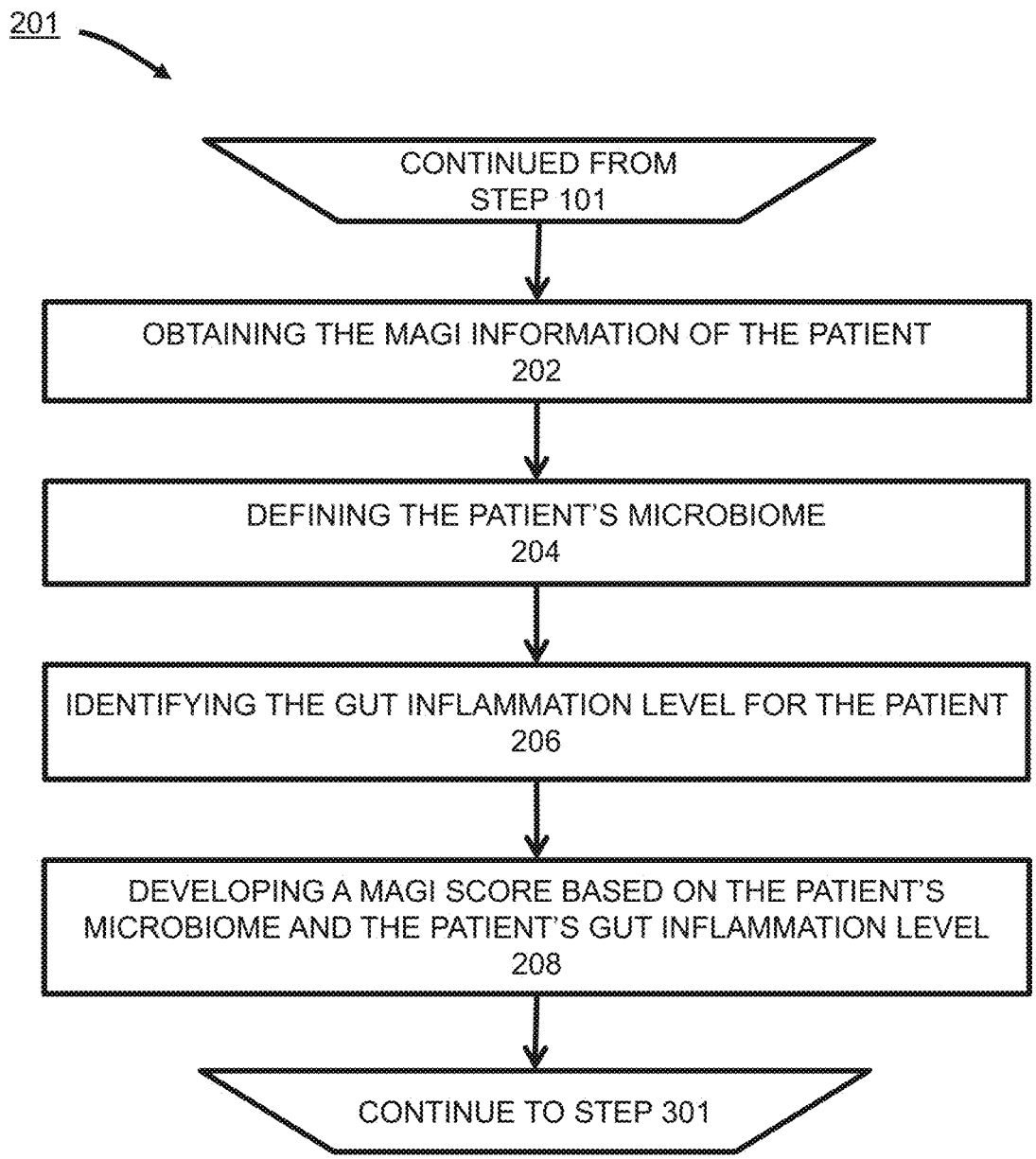
FIG. 4 is a flow chart illustrating the steps of a certain preferred embodiment of a method of the present invention by which a MAGI score may be developed from MAGI information.

FIG. 4 is a flowchart illustrating the steps of a certain embodiment of a method according to the present invention by which a certain microbiome-based action component—a MAGI score—may be developed from the MAGI information. The operation is continued from step 101, one embodiment of which is shown in FIG. 3. In step 202, the MAGI information developed for a patient is obtained. The MAGI information may include the revised MAGI information developed in step 116 of FIG. 3. In step 204, the patient's microbiome will be defined. In step 206, the gut inflammation level for the patient will be identified through use of a genetic and/or biochemical marker. In step 208, a MAGI score will be developed for the patient based on the gut inflammation level and the microbiome of the patient.

Figure 7A:
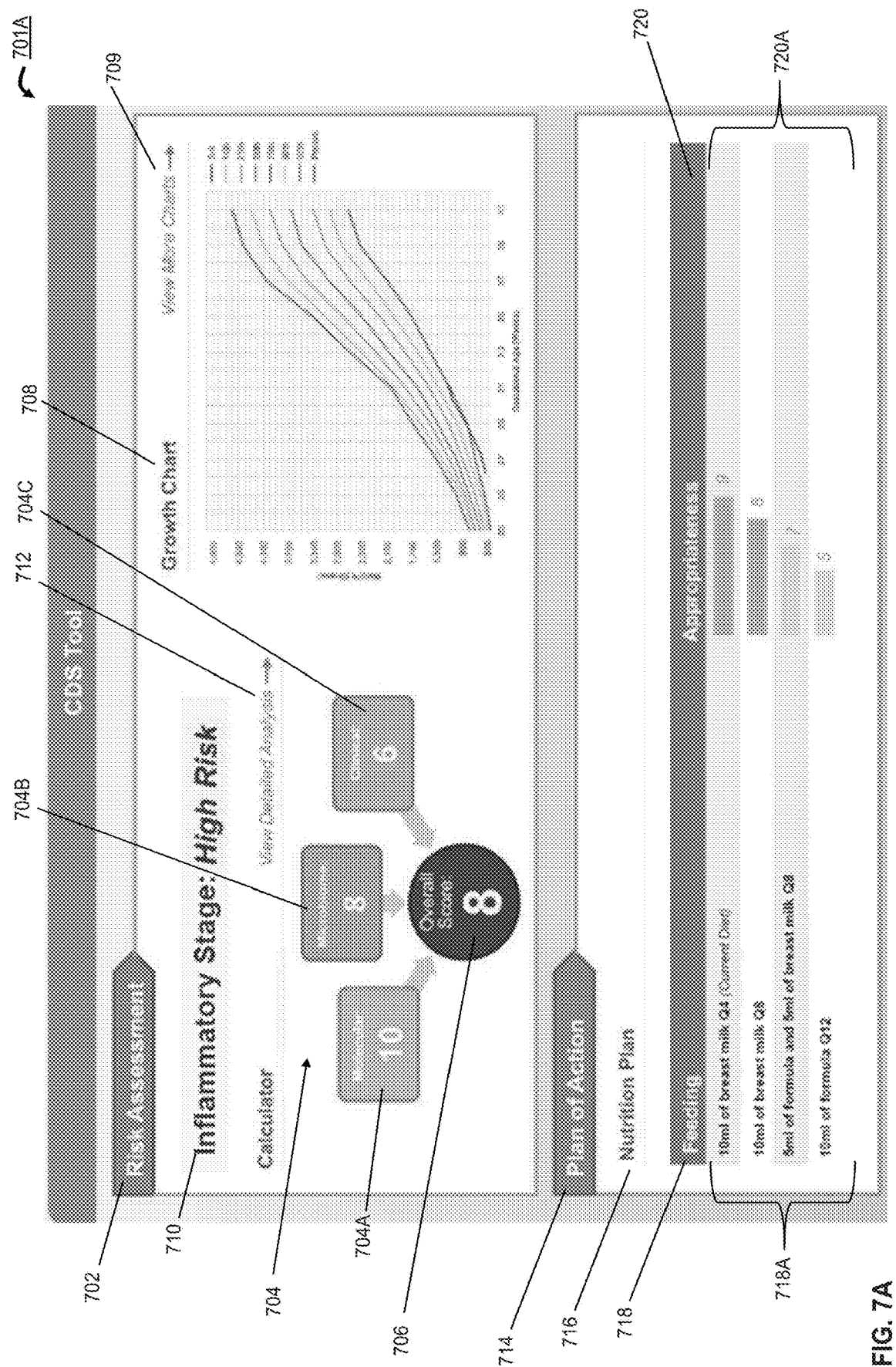
FIG. 7A is an image illustrating a certain preferred embodiment of a display of information developed according to the present invention and that may be provided to a user.
Figure 7B:
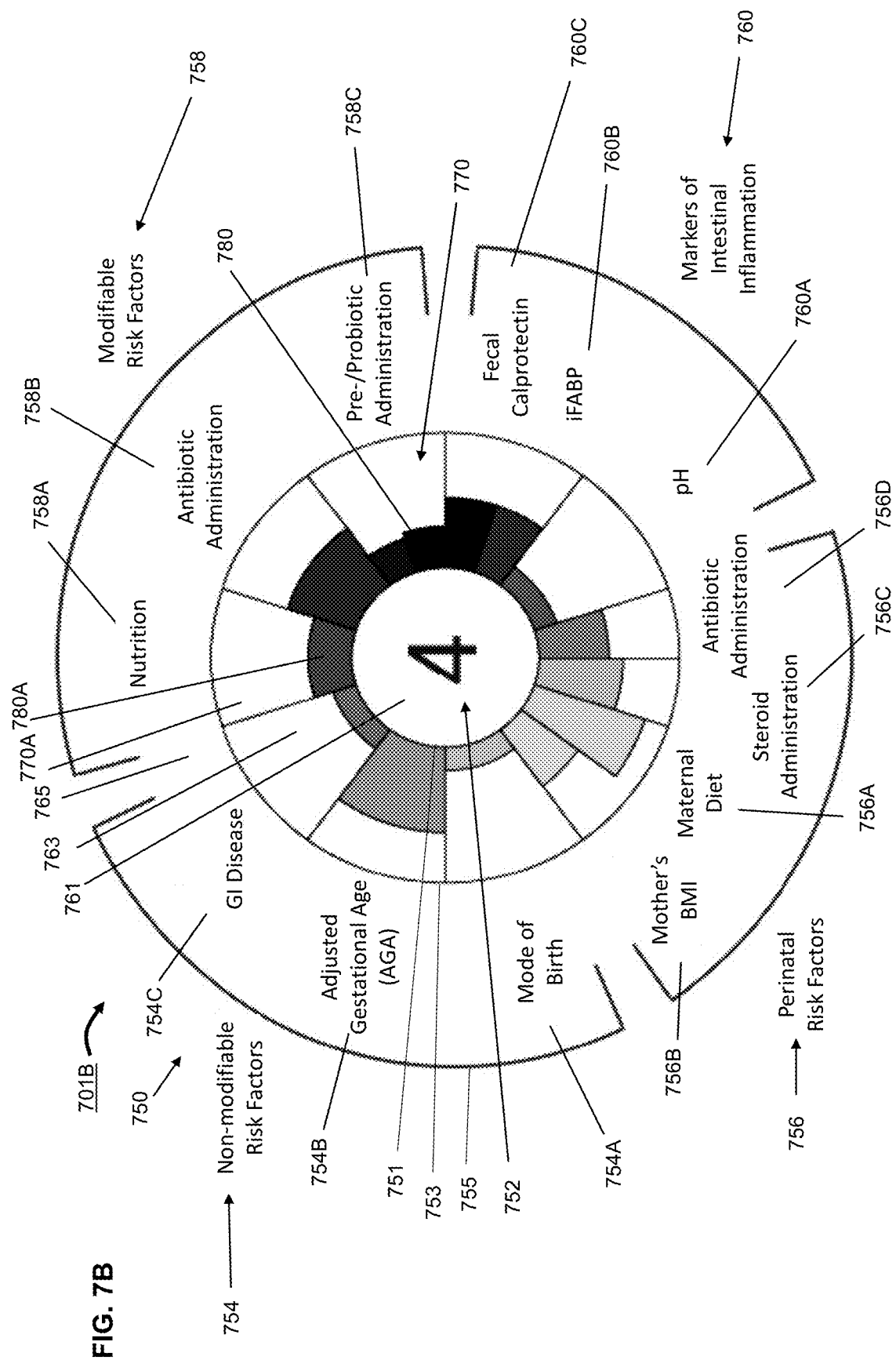
FIG. 7B is an image illustrating a certain preferred embodiment of another display of information developed according to the present invention and that may be provided to a user.

In step 301, the MAGI score may be displayed on display device 70. FIG. 7A shows one preferred embodiment of a display of the MAGI score. FIG. 7B shows another preferred embodiment of a display of the MAGI score. The value of the MAGI score may be represented through a variety of means, including a numerical value, an alphabet, letter, or word value, a symbol, or a combination of two or more such representations. If the development and output of an additional microbiome-based action component—personalized microbiome health plan—is desired, the operation will continue to step 401, shown in FIG. 2B and FIG. 5.

Figure 5:
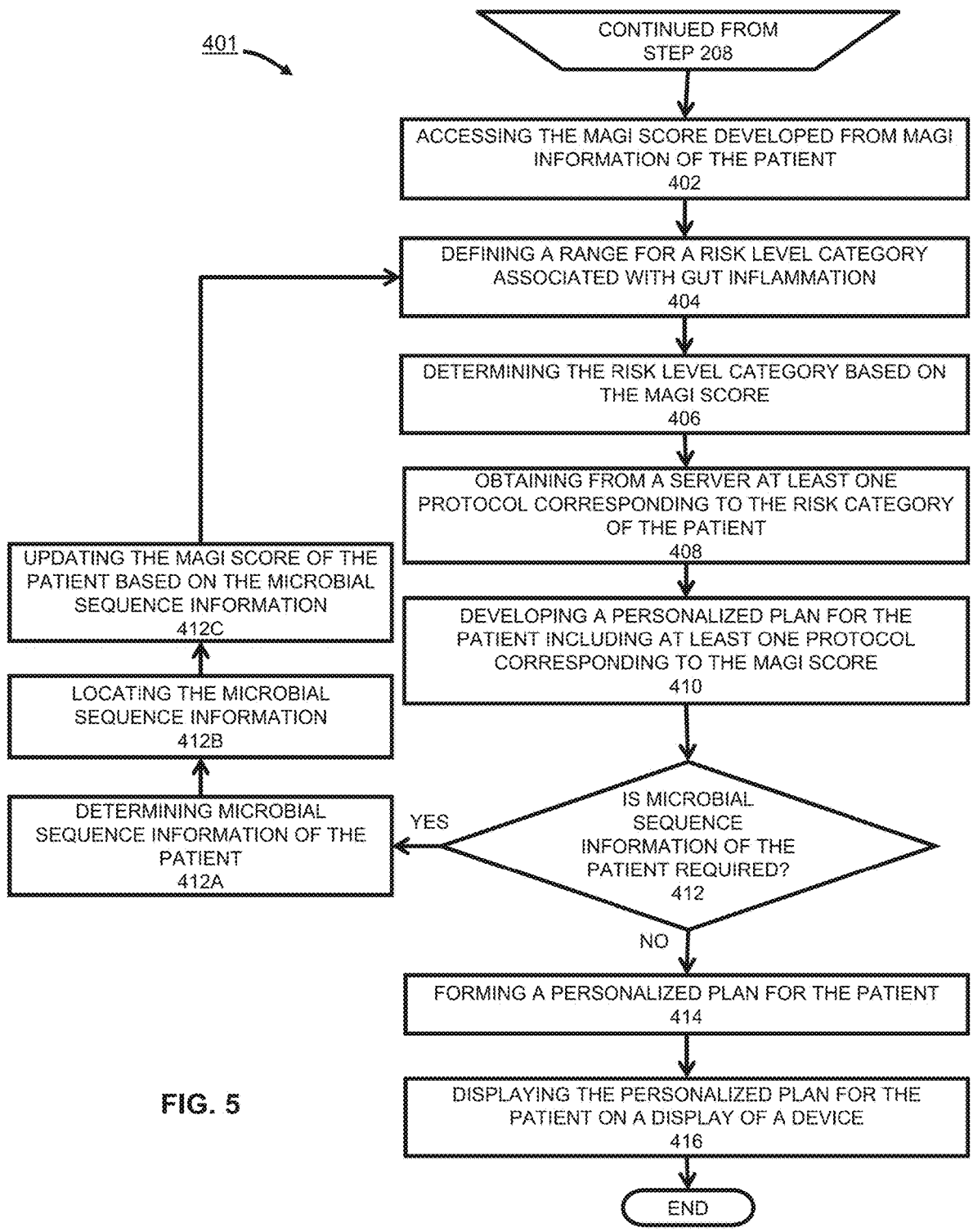
FIG. 5 is a flow chart illustrating the steps of a certain preferred embodiment of a method of the present invention by which a personalized microbiome health plan may be developed.

FIG. 5 is a flowchart 401 illustrating the steps of a certain preferred embodiment of a method according to the present invention by which a personalized microbiome health plan may be developed. The operation is continued from step 208 shown also in FIG. 4. In step 402, a MAGI score of a patient—developed through the use of the MAGI information of the patient—is accessed. The system 50 may store a number of protocols that have been prepared for different MAGI scores.

In step 404, a range for predicting propensity for gut inflammation will be defined for the patient. A range may include MAGI scores associated with a gut inflammation risk level category. The MAGI score may be used to determine the category of risk corresponding to the predefined range. The predefined range may be associated with the severity of the patient's condition. In step 406, the MAGI score will be used to determine the gut inflammation risk level category for the patient. In certain preferred embodiments, the risk level category may be identified through terms such as "low", "moderate", and "high".

In step 408, at least one protocol corresponding to the MAGI score of the patient is obtained—such as from a database in the server. A protocol may be one which a regulating authority, government agency, clinical trials or any other accepted method or organization in the health community develops. In certain preferred embodiments, one or more protocols may be generated by the system. Preferred embodiments of a protocol may also include suggested procedures that a health care professional, caretaker, or the patient may follow. For example, a protocol may include care components in which a caretaker may exercise discretion in attending to a patient, while another protocol may suggest that a caretaker follow an established sequence of actions. A protocol may also include rules and procedures that are specific to the training and certification of a caretaker. Further, a protocol may include sub-protocols that may be used in comprehensive protocols. For example, a sub-protocol may be included that concerns the patient's nutrition and suggest certain feeding activities for the patient. Protocols may further suggest the degree to which specific treatment be administered. Specified schedules and timers for taking an action (e.g. administering a treatment) may also be included in a protocol.

In step 410, a personalized microbiome health plan may be developed for the patient that includes the at least one protocol corresponding to the MAGI score. More than one protocol may exist for a particular MAGI score, and each protocol may include one or more sub-protocols corresponding to the MAGI score. The personalized microbiome health plan will be specific to the patient based on the calculated MAGI score calculated, for example, through the use of the steps 201 shown in FIG. 4. Accordingly, the protocols will be tailored to the condition and MAGI information of the patient.

In step 412, it will be determined whether microbial sequence information of the patient is required based on comparing the gut inflammation threshold to the MAGI score. Microbial sequence information may include a patient's functional information and biological sequence/structure information, including without limitation genomic sequence information, mRNA sequence information, protein sequence information, and information on secondary and tertiary structures.

If microbial sequence information is not required a personalized microbiome health plan will be formed for the patient in step 414. The personalized microbiome health plan may include at least one protocol corresponding to the patient's MAGI score. In step 416, the personalized microbiome health plan for the patient may be displayed on a display of a device. FIG. 7A illustrates a display providing such personalized microbiome health plan.

If, at step 412, the microbial sequence information of the patient is required, in step 412A, the microbial sequence information of the patient will be determined. The microbial sequence information may be stored in the system 50 or in any server accessible to the system 50. In step 412B, the microbial sequence information will be located from the server. In step 412C, the MAGI score of the patient will be updated using the microbial sequence information and the process reverts back to step 404.

FIG. 6A is a flowchart 401A illustrating the steps of a certain preferred embodiment according to the present invention by which for displaying a personalized microbial health plan, particularly for a premature infant, may be developed and displayed. The operation is continued from step 208 shown in FIG. 4. In step 422, the MAGI score—developed through the use of the MAGI information for the patient—is obtained. In step 426, a threshold score for developing a gastrointestinal or other condition is defined. In step 427, it will be determined whether the MAGI score of the patient is greater than the threshold score by comparison.

If the patient's MAGI score is greater than the threshold score at step 427, in step 430, a microbial profile for the patient will be determined. A microbial profile may include taxonomic and/or phylogenetic identification of the microbes in a biological community. A microbial profile can also include quantitative information about one or more microorganisms that have been identified in the microbial community. Microbial profiles may be in various forms, such as a list, graph, table, or any other appropriate representation of microorganisms in a community. A microbial profile may be used for identifying pathogenic and non-pathogenic microbial organisms in biological and non-biological samples. A microbial profile may be determined using any of a number of methods. For example, microbes in a biological sample can be genetically sequenced and colonies identified. Once the microbial profile of the premature infant is determined, in step 432, the microbial profile of the patient is accessed. In step 434, the microbial profile of the patient is analyzed.

If the MAGI score is less than the threshold score at step 428 or, once the microbial profile of the patient is analyzed at step 434, in step 436, it will be determined whether there is a high risk of disease or inflammation. If there is a high risk of disease at step 436, a protocol for early intervention will be developed for the patient in step 438. An early intervention protocol may include administration of a microbial agent, intravenous nutrition, and/or intravenous hydration. In certain embodiments, the microbial agents may be one or more prebiotic or probiotic formulations. If at step 436, there is not a high risk of disease, a feeding protocol to maximize growth, maintain, or optimize health will be produced for the patient in step 440. A feeding protocol may include a change in diet and/or a change in the rate of the feeding. For example, if there is not a high risk of disease for the patient, there may be an increase in the feeding rate for the patient. In step 442, a personalized microbiome health plan will be formulated for the premature infant patient. The personalized microbiome health plan may include a protocol based on the inflammatory risk level associated with the patient. In step 444, the personalized microbiome health plan for the patient may be displayed on a display of a device.

Figure 6B:
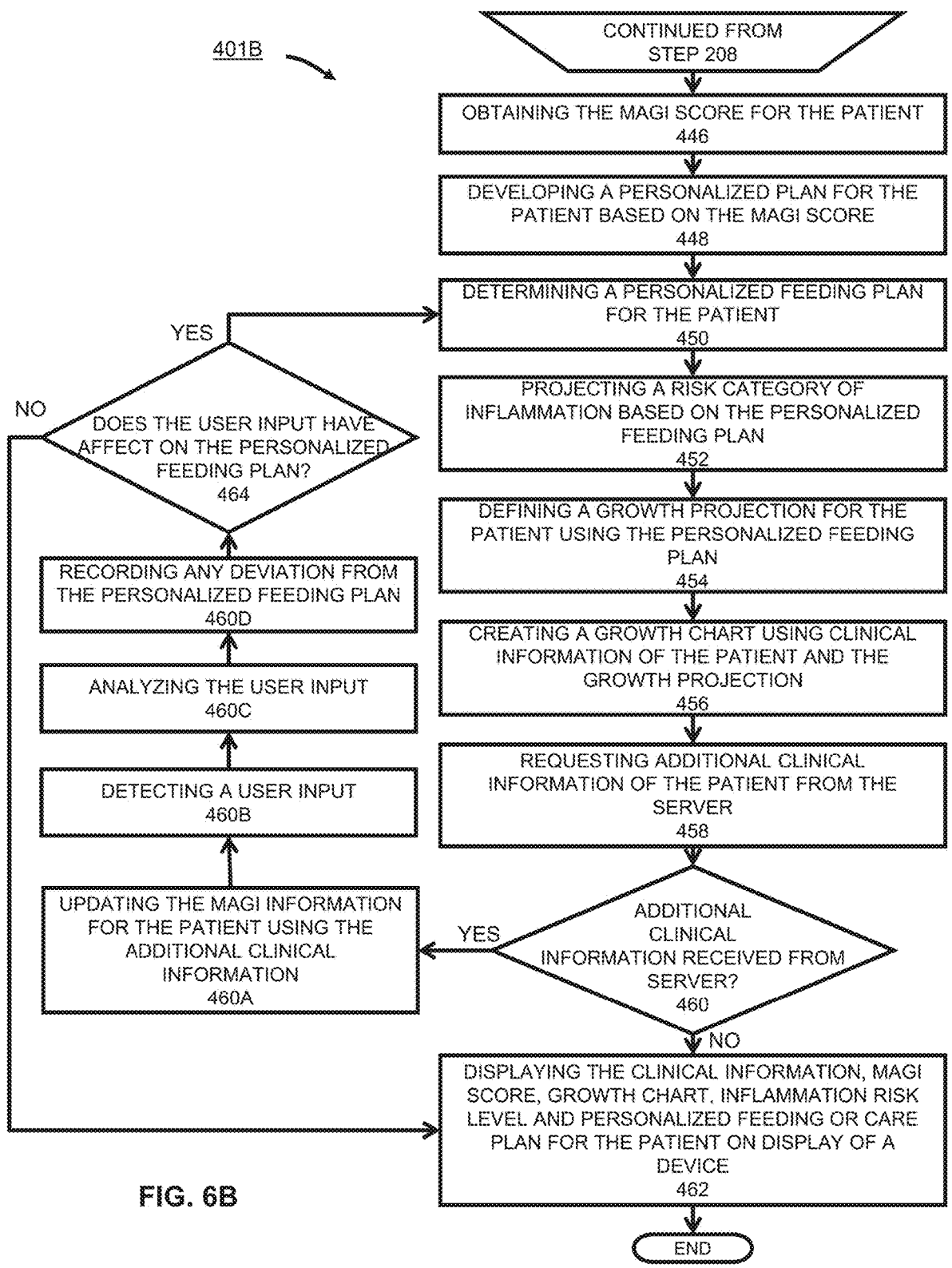
FIG. 6B is a flow chart illustrating the steps of a certain preferred embodiment of a method of the present invention by which a personalized microbial health plan may be developed based on new clinical and other information and displayed.

FIG. 6B is a flowchart providing more detail of step 301 of FIG. 2, in accordance with an embodiment of the system 50. The operation is continued from step 208. In step 446, the MAGI score for the patient is obtained. In step 448, a personalized microbiome health plan is developed for the patient based on the MAGI score. In step 450, a personalized feeding plan is determined for the patient. In step 452, a risk category of gut inflammation or disease is projected based on the personalized feeding plan. In step 454, a growth projection for the patient is defined using the personalized feeding plan. In certain embodiments, system 50 may include a growth module to generate a growth projection. The growth projection may be defined using a number of variables associated with the feeding plan. For example, the type of nutrition, the amount of nutrition, and the frequency of feeding may be used to project growth. In step 456, a growth chart is created using clinical information of the patient and the growth projection.

In step 458, additional clinical information of the patient is requested from the server. In step 460, the system 50 will determine whether additional information was received from the server. If no additional information is received at step 460, the microbial health risk factor information, MAGI score, growth chart, inflammatory risk level and personalized feeding plan may be displayed on a display of a device in step 462.

If, at step 460, the system 50 determines that the additional clinical information was received from the server, in step 460A, the system 50 may update the MAGI information for the patient using the additional clinical information. The additional MAGI information may be input by a device that is configured by a user. In step 460B, the system 50 will detect the user input. In step 460C, the system 50 will analyze the user input. In step 460D, the system will record any deviation by the user from the personalized feeding plan. In step 464, the system 50 will determine whether the user input has an effect on the personalized feeding plan. If the user input does have an effect on the personalized feeding plan at step 464, the operation reverts back to step 450. If the user input does not have an effect on the personalized feeding plan at step 464, the operation will proceed to step 462.

FIG. 7A is an image illustrating a certain preferred embodiment of a display of information developed according to the present invention that may be provided to a user. In FIG. 7A, the exemplary dashboard display 701A provides a risk assessment view 702 and associated protocols 718 for a patient. The illustrated embodiment of risk assessment view 702 includes certain MAGI information 704, a MAGI score 706, a growth chart 708, and an inflammatory risk level category 710. Additional detailed information may be shown in response to a user selecting the "View Detailed Analysis" option 712, which will provide additional information, such as the illustrated Growth Chart 708 or more information through engaging the area entitled "View More Charts" 709. The illustrated embodiment of the display 701A provides information how the MAGI score 706 was calculated from the MAGI information 704 which is displayed. Within the risk assessment view 702, the certain MAGI information 704 provided in this certain preferred embodiment is shown "Molecular" 704A, "Microbiome" 704B, and "Clinical" 704C. These are shown with the values, "10", "8", and "6", respectively. Exemplary dashboard display 701A provides the user with the MAGI score 706 calculated by processor 60 using the MAGI information. The exemplary dashboard display 701A also provides a plan of action view 714 for the patient based on the information in a risk assessment view 702. In the plan of action view 714, one or more protocols may be displayed corresponding to a patient's MAGI score 706 displayed in the risk assessment view 702. For example, the plan of action view 714 of example dashboard display 701A provides a user with a "Nutrition Plan" entry 716. The illustrated embodiment of the Nutrition Plan entry 716 proposes Feeding information 718 for the patient. Specifically, in the illustrated embodiment of the display 701A, Feeding information 718 provides feeding protocols 718A for the patient, in the illustrated example, an infant. The illustrated plan of action view 714 also provides information regarding the possible effectiveness of the proposed feeding protocols in "Appropriateness" area 720. A protocol may be determined to be effective through various techniques. For example, previously used protocols that have not produced healthy patient results may be deemed to be less effective as compared to protocols that have shown an improvement in a patient's health. For each of the Feeding protocols, the illustrated embodiment of the Appropriateness information 720 identifies effectiveness through numerical rankings 720A.

FIG. 7B is an image illustrating a certain preferred embodiment of another display of information developed according to the present invention that may be provided to a user. In FIG. 7B, an exemplary dashboard display 701B is shown that provides an exemplary MAGI score 752, in accordance with an embodiment of the invention. Exemplary dashboard display 701B may be provided on a display device. Exemplary dashboard display 701B provides the MAGI score view 752 for a patient, the non-modifiable risk factors for the patient 754, the modifiable risk factors 758, the perinatal risk factors 756, the markers of intestinal inflammation 760 and the associated weighting of each element 770 in calculation of the MAGI score. Additional detailed information may be shown in response to a user selecting the "Risk Factors" option 754, 756, and 758, which will provide additional information regarding the various microbial health risk factors used in calculating the MAGI score. Within the illustrated embodiment of the MAGI score view 752, Non-modifiable Risk Factors 754 is broken down into the following information components: "Mode of Birth" 754A, "Adjusted Gestational Age" 754B, and "GI Disease" 754C. In the illustrated embodiment, Perinatal Risk Factors 756 is broken down into the following information components: "Maternal Diet" 756A, "Mothers Body Mass Index (BMI)" 756B, and "Steroids Administration" 756C, and "Antibiotics Administration" 756D. In this illustrated embodiment, Modifiable Risk Factors 758 which is broken information components into "Nutrition" 758A, "Antibiotic Administration" 758B, and "Pre-/Probiotics Administration" 758C. Modifiable Risk Factors could include the Feeding Plan 718 or the Nutrition Plan 716. Within the MAGI score view 701B, "Markers of Intestinal Inflammation" 760 may be broken down to information components such as the illustrated "pH" 760A, "iFABP" 760B, and "Fecal Calprotectin" 760C as exemplary molecular markers of gut inflammation. In the Illustrated process, the microbial health risk factors and markers of inflammation are weighted 770 to show each element's impact on the calculation of the MAGI score 752. One embodiment by which a MAGI score may be produced is the following:

$$f_1 w_1 + f_2 w_2 + f_3 w_3 + \ldots = \text{MAGI score}$$

in which the "f" factors are the microbial health risk factors and the "w" factors are the weightings corresponding to that factor's impact on the state of health as determined by the System. The sum of the individual factors multiplied by each corresponding weighting is totaled to provide the MAGI score.

As shown in FIG. 7B, the dashboard display 701B comprises a graphical user interface 750 summarizing a state of the patient's microbiome and risk of inflammation. The graphical user interface 750 comprises concentric circles 751, 753, 755 forming a center circle 761, a first annulus 763, and a second annulus 765. The center circle 761 includes the calculated patient MAGI score 752. The first annulus 763 includes a plurality of pie chart elements 770, and the second annulus 765 identifies the factors—754A, 754B, 756A, 756C, etc.—of each category 754, 756, 758, 760 of the MAGI information.

Each factor—754A, 754B, 756A, 756C, etc.—corresponds to a pie chart element 770 of the first annulus 763. And a size of each pie chart element 770 is representative of the weight value of the corresponding factor—754A, 754B, 756A, 756C, etc.—on the MAGI score. Each pie chart element 770 further includes a bar chart element 780. The length of the bar chart element 780 is representative of an impact of the factor on the calculated patient MAGI score.

For example, a "Nutrition" 758A factor of the Modifiable Risk Factor Category 758 corresponds to pie chart element 770A with bar chart element 780A. As seen, the size of the pie chart element 770A is greater than the size of the pie chart element for "Steriod Administration" 756C and the length of the bar chart element 780A is less than the bar chart element for "Steriod Administration" 756C. Therefore, while "Nutrition" 758A has a greater weight value than "Steroid Administration" 756C on the MAGI score, "Nutrition" 758A nevertheless has less of an overall impact than "Steroid Administration" 756C on the calculated MAGI score for the patient because the "Nutrition" 758A factor is less than the "Steroid Administration" 756C factor.

A user can interrogate any element of the calculation to see its native value or state as well as its weighting factor for calculating the MAGI score.

Figure 8:
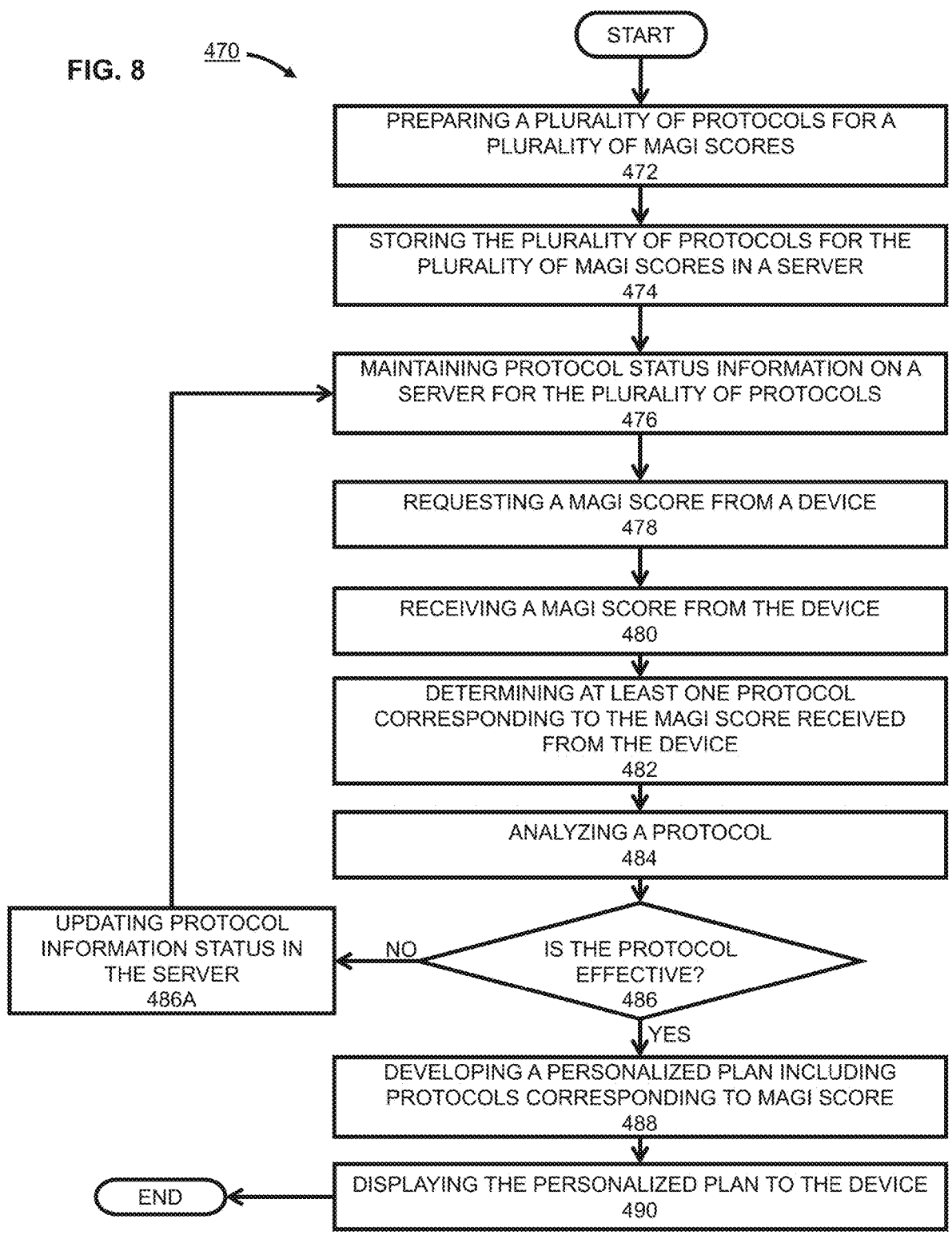
FIG. 8 is a flow chart illustrating the steps of a certain preferred embodiment of a method of the present invention by which a plurality of protocols may be developed and made accessible for use in conjunction with a plurality of MAGI scores.

FIG. 8 is a flowchart 470 illustrating the steps of a certain preferred embodiment according to the present invention by which a plurality of protocols may be developed and made accessible for use in conjunction with a plurality of microbiome and gut inflammation (MAGI) scores. The method begins and in step 472, a plurality of protocols is prepared for a plurality of MAGI scores. In step 474, the plurality of protocols for the plurality of MAGI scores is stored in a server. In step 476, protocol status information is maintained on a server for the plurality of protocols. The protocol status information may include information indicating whether a protocol was effective for a corresponding MAGI score. An effective protocol may include a protocol that corresponds to a personalized microbiome health plan, which has been previously administered to a patient and provided successful results (i.e. the patient has shown signs of recovery and/or healthy development). In step 478, the server will request a MAGI score from a device and in step 480 the server will receive a MAGI score from the device. In step 482, at least one protocol corresponding to the received MAGI score will be determined. In step 484, the at least one protocol will be analyzed. The protocol may be analyzed based on a number of factors. For example, the protocol may be analyzed based on a healthy patient result has been associated with the protocol. In another example, the protocol may be analyzed based on new clinical information, literature, and/or case studies. In step 486, the server will determine if a protocol is effective. If the protocol is effective at step 486, in step 488, a personalized microbiome health plan will be developed including protocols corresponding to the MAGI score. The personalized microbiome health plan may include only effective protocols or may include all protocols corresponding to the MAGI score with indicators for protocols that are not effective. In step 490, the personalized plan will be sent to the device for display. If at step 486, a protocol is not effective, in step 486A, protocol information status in the database will be updated to indicate that the protocol is not effective. The operation will revert back to step 476.

Figure 9:
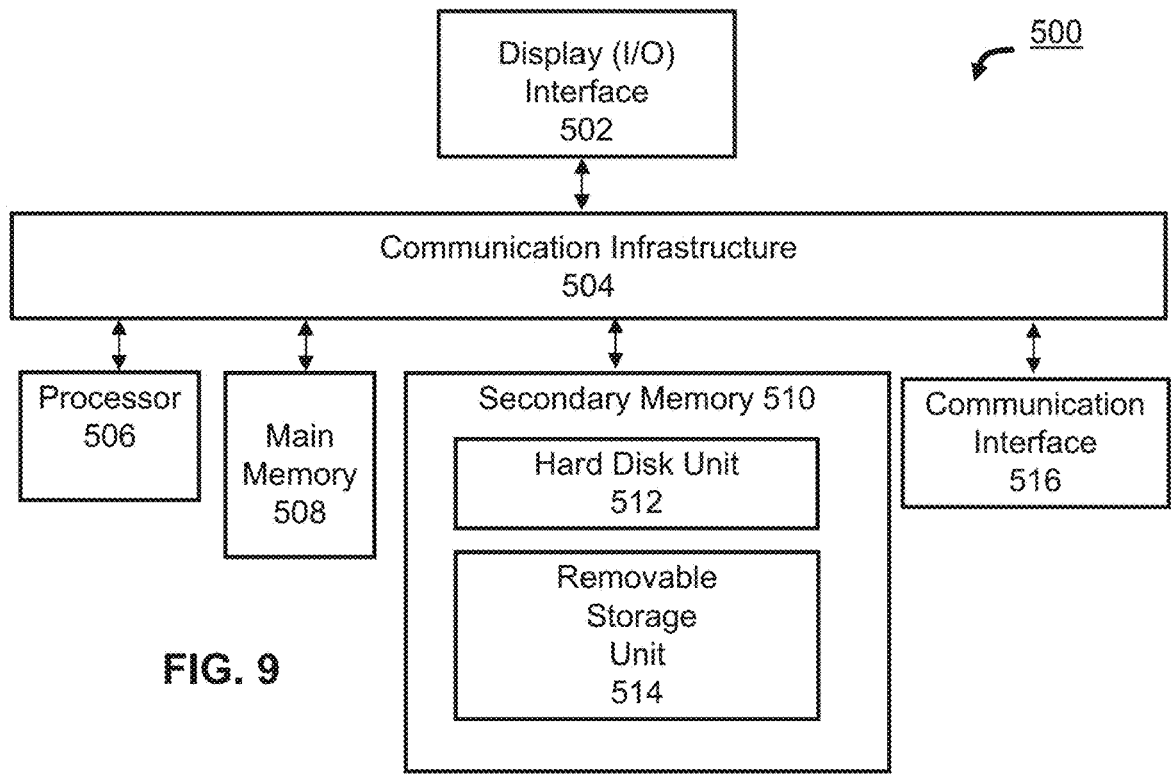
FIG. 9 is an exemplary computing system that may be used for implementation of all or a portion of the invention.

FIG. 9 illustrates an exemplary computer system 500 that may be used to implement the methods according to the present invention. One or more computer systems 500 may carry out the present invention according to processing instructions, or computer code.

Computer system 500 includes an input/output display interface 502 connected to communication infrastructure 504—such as a bus—which forwards data such as graphics, text, and information, from the communication infrastructure 504 to other components of the computer system 500. The input/output display interface 502 may be the display device 70 (FIG. 1) or, alternatively, a speaker, printer, any other computer peripheral device, or any combination thereof, capable of communicating an area of interest. Furthermore, the interface 502 may be a keyboard, joystick, trackball, and mouse for the user to enter what he or she believes to be an area of interest.

One or more processors components 506 such as processor component 60 (FIG. 1) may be a special purpose or a general-purpose digital signal processor that processes certain information. Computer system 500 may also include a main memory 508, for example random access memory ("RAM"), read-only memory ("ROM"), mass storage device, or any combination of tangible, non-transitory memory as well as a secondary memory 510 such as a hard disk unit 512, a removable storage unit 514, or any combination of tangible, non-transitory memory.

Computer system 500 may also include a communication interface 516, for example, a modem, a network interface (such as an Ethernet card or Ethernet cable), a communication port, a PCMCIA slot and card, wired or wireless systems (such as Wi-Fi®, Bluetooth®, Infrared), local area networks, wide area networks, intranets, etc. Communication interface 516 allows software, instructions and data to be transferred between the computer system 500 and external devices or external networks.

Computer programs, when executed, enable the computer system 500, particularly the processor 506, to implement the methods of the invention according to computer software instructions. The computer system 500 of FIG. 9 is provided only for purposes of illustration, such that the invention is not limited to this specific embodiment. It is appreciated that a person skilled in the relevant art knows how to program and implement the invention using any computer system.

The computer system 500 may be a handheld device and include any small-sized computer device including, for example, a personal digital assistant ("PDA"), smart handheld computing device, cellular telephone, or a laptop or netbook computer, hand held console or MP3 player, tablet, or similar hand held computer device, such as an iPad®, iPad Touch® or iPhone®.

Figure 10:
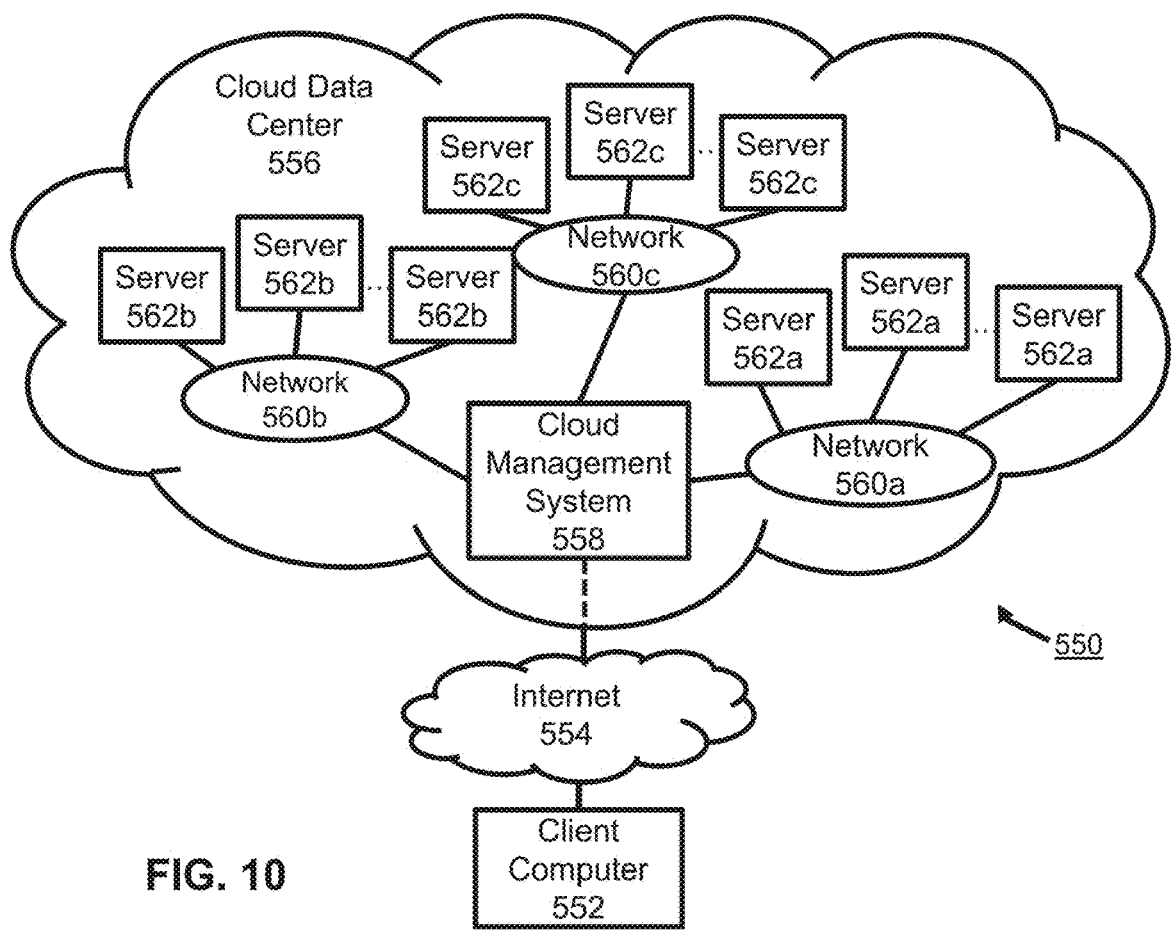
FIG. 10 is an exemplary cloud computing system that may be used for implementation of all or a portion of the invention.

Separate and apart from, or in addition to, computer system 500, the methods according to the invention may be implemented using a cloud computing system. FIG. 10 illustrates an exemplary cloud computing system 550 that may be used to implement the methods according to the invention. The cloud computing system 550 includes a plurality of interconnected computing environments. The cloud computing system 550 utilizes the resources from various networks as a collective virtual computer, where the services and applications can run independently from a particular computer or server configuration making hardware less important.

Specifically, the cloud computing system 550 includes at least one client computer 552. The client computer 552 may be any device through the use of which a distributed computing environment may be accessed to perform the methods disclosed herein, for example, the computer described above in FIG. 9, a portable computer, mobile phone, personal digital assistant, tablet to name a few. Signals are transferred between the client computer 552 and external devices including networks such as the Internet 554 and cloud data center 556. Communication may be implemented using wireless or wired capability such as cable, fiber optics, a phone line, a cellular phone link, radio waves or other communication channels.

The client computer 552 establishes communication with the Internet 554—specifically to one or more servers—to, in turn, establish communication with one or more cloud data centers 556. A cloud data center 556 includes one or more networks 560a, 560b, 560c managed through a cloud management system 558. Each network 560a, 560b, 560c includes resource servers 562a, 562b, 562c, respectively. Servers 562a, 362b, 362c permit access to a collection of computing resources and components that can be invoked to instantiate a virtual computer, process, or other resource for a limited or defined duration. For example, one group of resource servers can host and serve an operating system or components thereof to deliver and instantiate a virtual computer. Another group of resource servers can accept requests to host computing cycles or processor time, to supply a defined level of processing power for a virtual computer. A further group of resource servers can host and serve applications to load on an instantiation of a virtual computer, such as an email client, a browser application, a messaging application, or other applications or software.

The cloud management system 558 may be configured to query and identify the computing resources and components managed by the set of resource servers 562*a*, 562*b*, 562*c* needed and available for use in the cloud data center 556. Specifically, the cloud management system 558 may be configured to identify the hardware resources and components such as type and amount of processing power, type and amount of memory, type and amount of storage, type and amount of network bandwidth and the like, of the set of resource servers 562*a*, 562*b*, 562*c* needed and available for use in the cloud data center 556. Likewise, the cloud management system 558 can be configured to identify the software resources and components, such as type of Operating System ("OS"), application programs, and the like, of the set of resource servers 562*a*, 562*b*, 362*c* needed and available for use in the cloud data center 556.

The cloud computing system 550 of FIG. 10 is provided only for purposes of illustration and does not limit the invention to this specific embodiment. It is appreciated that a person skilled in the relevant art knows how to program and implement the invention using any computer system or network architecture.

While the invention is susceptible to various modifications and alternative forms, specific exemplary embodiments of the invention have been shown by way of example in the drawings and have been described in detail. It should be understood, however, that there is no intent to limit the invention to the particular embodiments disclosed, but on the contrary, the intention is to cover all modifications, equivalents, and alternatives falling within the scope of the invention as defined by the appended claims.

What is claimed is:

1. A computer program stored in one or more non-transitory computer-readable mediums for generating a graphical user interface identifying a state of a patient's microbiome and risk of inflammation, the computer program comprising instructions for performing the steps of:
   accessing by a processor microbiome and gut inflammation (MAGI) information of a patient, the MAGI information consisting of categories: (a) non-modifiable risk factors, (b) modifiable risk factors, (c) perinatal risk factors, and (d) markers of intestinal inflammation;
   providing by the processor a MAGI score equation, wherein the MAGI score=$f_1 w_1 + f_2 w_2 + f_3 w_3 + f_x w_x$, wherein "f" is a factor within the categories of the MAGI information and "w" is a weight value, wherein each weight value corresponds to an impact of the factor on the MAGI score;
   calculating by the processor a patient MAGI score using the MAGI information of the patient; and
   displaying by the processor on a display a graphical user interface summarizing a state of the patient's microbiome and a risk of inflammation, wherein the graphical user interface comprises a plurality of concentric circles, the plurality forming a center circle that includes the calculated patient MAGI score, a first annulus that includes a plurality of pie chart elements, and a second annulus that identifies the factors, a size of each pie chart element representative of the weight value of the corresponding factor on the MAGI score, each pie chart element including a bar chart element representative of an impact of the factor on the calculated patient MAGI score.

2. The computer program stored in one or more non-transitory computer-readable mediums for generating a graphical user interface identifying a state of a patient's microbiome and risk of inflammation of claim 1, wherein the factors identified in the second annulus for the non-modifiable risk factors category includes the factors: mode of birth, adjusted gestational age, and GI disease.

3. The computer program stored in one or more non-transitory computer-readable mediums for generating a graphical user interface identifying a state of a patient's microbiome and risk of inflammation of claim 1, wherein the factors identified in the second annulus for the perinatal risk factors category includes the factors: maternal diet, mother's body mass index (BMI), steroid administration, and antibiotics administration.

4. The computer program stored in one or more non-transitory computer-readable mediums for generating a graphical user interface identifying a state of a patient's microbiome and risk of inflammation of claim 1, wherein the factors identified in the second annulus for the modifiable risk factors category includes the factors: nutrition, antibiotic administration, pre-/probiotics administration.

5. The computer program stored in one or more non-transitory computer-readable mediums for generating a graphical user interface identifying a state of a patient's microbiome and risk of inflammation of claim 1, wherein the factors identified in the second annulus for the intestinal inflammation category includes the factors: pH, intestinal fatty acid binding-protein ("iFABP"), and fecal calprotectin.

6. The computer program stored in one or more non-transitory computer-readable mediums for generating a graphical user interface identifying a state of a patient's microbiome and risk of inflammation of claim 1, further comprising the step of:
   selecting by the processor a protocol from a plurality of protocols, wherein the selected protocol corresponds to the calculated patient MAGI score; and
   displaying by the processor on the display the selected protocol.

7. The computer program stored in one or more non-transitory computer-readable mediums for generating a graphical user interface identifying a state of a patient's microbiome and risk of inflammation of claim 1, wherein the MAGI score is based on a scale 1-10, wherein the MAGI score of 1-3 associated with a low risk for the patient to develop an inflammatory state, the MAGI score of 4-6 associated with a moderate risk for the patient to develop an inflammatory state, and the MAGI score of 7-10 associated with a high risk for the patient to develop an inflammatory state.

* * * * *